(12) United States Patent
Kim (10) Patent No.: US 9,189,471 B2
(45) Date of Patent: Nov. 17, 2015

(54) APPARATUS AND METHOD FOR RECOGNIZING EMOTION BASED ON EMOTIONAL SEGMENTS

(71) Applicant: Samsung Electronics Co., Ltd., Suwon-si (KR)

(72) Inventor: Hyun-Jun Kim, Osan-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 68 days.

(21) Appl. No.: 13/680,038

(22) Filed: Nov. 17, 2012

(65) Prior Publication Data

US 2013/0132088 A1    May 23, 2013

(30) Foreign Application Priority Data

Nov. 18, 2011 (KR) .......................... 10-2011-0121173

(51) Int. Cl.
*G06F 17/27* (2006.01)
*A61B 5/16* (2006.01)

(52) U.S. Cl.
CPC .............. *G06F 17/27* (2013.01); *A61B 5/165* (2013.01)

(58) Field of Classification Search
CPC .............................. G10L 17/26; G10L 15/265
USPC .......................... 704/231–250, 270, 273, 274
See application file for complete search history.

(56) References Cited

U.S. PATENT DOCUMENTS

| | | | | |
|---|---|---|---|---|
| 5,577,165 A * | 11/1996 | Takebayashi et al. | ........ | 704/275 |
| 6,151,571 A * | 11/2000 | Pertrushin | ..................... | 704/209 |
| 6,275,806 B1 * | 8/2001 | Pertrushin | ..................... | 704/272 |
| 6,697,457 B2 * | 2/2004 | Petrushin | ................... | 379/88.08 |
| 7,222,075 B2 * | 5/2007 | Petrushin | ...................... | 704/270 |
| 7,451,079 B2 * | 11/2008 | Oudeyer | ....................... | 704/205 |
| 7,590,538 B2 * | 9/2009 | St. John | ........................ | 704/246 |
| 2001/0056349 A1 * | 12/2001 | St. John | ........................ | 704/270 |
| 2002/0002460 A1 * | 1/2002 | Pertrushin | ..................... | 704/270 |
| 2002/0194002 A1 * | 12/2002 | Petrushin | ..................... | 704/270 |
| 2003/0033145 A1 * | 2/2003 | Petrushin | ..................... | 704/236 |
| 2005/0273326 A1 * | 12/2005 | Padhi et al. | ................... | 704/231 |
| 2006/0167694 A1 * | 7/2006 | Mitsuyoshi | ................... | 704/270 |
| 2007/0162283 A1 * | 7/2007 | Petrushin | ..................... | 704/255 |
| 2007/0208569 A1 * | 9/2007 | Subramanian et al. | ....... | 704/270 |
| 2009/0055176 A1 * | 2/2009 | Hu et al. | ....................... | 704/240 |
| 2009/0265170 A1 | 10/2009 | Irie et al. | | |
| 2011/0172992 A1 | 7/2011 | Shin et al. | | |
| 2011/0178803 A1 * | 7/2011 | Petrushin | ..................... | 704/270 |
| 2011/0307257 A1 * | 12/2011 | Pereg et al. | ................... | 704/251 |
| 2012/0089396 A1 * | 4/2012 | Patel et al. | ..................... | 704/249 |

FOREIGN PATENT DOCUMENTS

| | | |
|---|---|---|
| JP | 2007-133227 A | 5/2007 |
| KR | 10-2004-0014123 A | 2/2004 |
| KR | 10-0829822 B1 | 5/2008 |

(Continued)

*Primary Examiner* — Douglas Godbold
(74) *Attorney, Agent, or Firm* — NSIP Law (57) ABSTRACT

An apparatus and method to recognize a user's emotion based on emotional segments are provided. An emotion recognition apparatus includes a sampling unit configured to extract sampling data from input data for emotion recognition. The emotion recognition apparatus further includes a data segment creator configured to segment the sampling data into a plurality of data segments. The emotion recognition apparatus further includes an emotional segment creator configured to create a plurality of emotional segments that include a plurality of emotions corresponding to each of the respective data segments.

21 Claims, 12 Drawing Sheets

(56) References Cited

FOREIGN PATENT DOCUMENTS

| KR | 10-2010-0086398 A | 7/2010 |
| KR | 10-1029786 B1 | 4/2011 |
| KR | 10-2011-0081659 A | 7/2011 |

* cited by examiner

| Emotion | S1 | S2 | S3 | S4 | S5 |
|---|---|---|---|---|---|
| Neutral | 51% | 40% | 85% | 66% | 73% |
| Anger | 67% | 56% | 33% | 38% | 29% |
| Happiness | 59% | 28% | 65% | 52% | 40% |
| Surprise | 44% | 73% | 29% | 31% | 35% |
| Sadness | 31% | 59% | 61% | 73% | 71% |
| Disgust | 50% | 81% | 22% | 62% | 76% |
| Fear | 48% | 47% | 50% | 48% | 52% |
| Emotion Segment | Anger | Disgust | Neutral | Sadness | Disgust |

| Emotion | S1 | S2 | S3 | S4 | S5 |
|---|---|---|---|---|---|
| Neutral | 51% | 40% | 85% | 66% | 73% |
| Anger | 67% | 56% | 33% | 38% | 29% |
| Happiness | 59% | 28% | 65% | 52% | 40% |
| Surprise | 44% | 73% | 29% | 31% | 35% |
| Sadness | 31% | 59% | 61% | 73% | 71% |
| Disgust | 50% | 81% | 22% | 62% | 76% |
| Fear | 48% | 47% | 50% | 48% | 52% |
| St. Dev. | 0.11 | 0.18 | 0.23 | 0.15 | 0.19 |

Window Confidence($\sigma$)
S1 = 0.11
S2 = 0.18
S3 = 0.23
S4 = 0.15
S5 = 0.19

FIG. 7B

| Emotion | S1 | S2 | S3 | S4 | S5 |
|---|---|---|---|---|---|
| Neutral | 51% | 40% | 85% | 66% | 73% |
| Anger | 67% | 56% | 33% | 38% | 29% |
| Happiness | 59% | 28% | 65% | 52% | 40% |
| Surprise | 44% | 73% | 29% | 31% | 35% |
| Sadness | 31% | 59% | 61% | 73% | 71% |
| Disgust | 50% | 81% | 22% | 62% | 76% |
| Fear | 48% | 47% | 50% | 48% | 52% |
| Entropy | 0.14 | 0.28 | 0.42 | 0.42 | 0.42 |

Entropy
S1 = 0.14
S2 = 0.28
S3 = 0.42
S4 = 0.42
S5 = 0.42

FIG. 7C

| Emotion | S1 | S2 | S3 | S4 | S5 |
|---------|-----|-----|-----|-----|-----|
| Neutral | 51% | 40% | 85% | 66% | 73% |
| Anger | 67% | 56% | 33% | 38% | 29% |
| Happiness | 59% | 28% | 65% | 52% | 40% |
| Surprise | 44% | 73% | 29% | 31% | 35% |
| Sadness | 31% | 59% | 61% | 73% | 71% |
| Disgust | 50% | 81% | 22% | 62% | 76% |
| Fear | 48% | 47% | 50% | 48% | 52% |
| St. Dev. | 0.11 | 0.18 | 0.23 | 0.15 | 0.19 |

Maximum Probability
S1 = 67%
S2 = 81%
S3 = 85%
S4 = 73%
S5 = 76%

Window Confidence($\sigma$)
S1 = 0.11
S2 = 0.18
S3 = 0.23
S4 = 0.15
S5 = 0.19

REPRESENTATIVE EMOTION(Max. Window Confidence)
[ Neutral ]

COMPLEX EMOTION(Window Confidence $\geq$ 0.18, Probability > 0.8)
[ Disgust ] + [ Neutral ]

CHANGED EMOTION (WITH ELAPSE OF TIME)

FIG. 8

APPARATUS AND METHOD FOR RECOGNIZING EMOTION BASED ON EMOTIONAL SEGMENTS

CROSS-REFERENCE TO RELATED APPLICATION

This application claims the benefit under 35 U.S.C. §119(a) of a Korean Patent Application No. 10-2011-0121173, filed on Nov. 18, 2011, in the Korean Intellectual Property Office, the entire disclosure of which is incorporated herein by reference for all purposes.

BACKGROUND

1. Field

The following description relates to an apparatus and method to recognize a user's emotion and provide an appropriate service according to the user's emotion.

2. Description of the Related Art

A user's emotion has been estimated based on direct information, such as the user's look or voice, from which the user's emotion can be directly recognized. In addition, a user's emotion has been estimated based on indirect information, such as the user's behavior pattern.

In recognizing a user's emotion at a specific time, a sufficient amount of successive data may be essential for a more exact recognition. However, there may be difficulties in accurately interpreting a user's emotional state from given data since a human's emotions tend to become complicated and often change. Moreover, data about successive direct/indirect human behaviors can include certain noise that may cause performance deterioration in emotion recognition.

SUMMARY

In one general aspect, there is provided an emotion recognition apparatus including a sampling unit configured to extract sampling data from input data for emotion recognition. The emotion recognition apparatus further includes a data segment creator configured to segment the sampling data into a plurality of data segments. The emotion recognition apparatus further includes an emotional segment creator configured to create a plurality of emotional segments that include a plurality of emotions corresponding to each of the respective data segments.

The data segment creator is further configured to segment the sampling data at regular intervals based on a predetermined time-domain window.

The data segment creator is further configured to segment the sampling data at different intervals based on two or more predetermined time-domain windows.

The data segment creator is further configured to reconfigure the sampling data based on a predetermined time-domain window such that a portion of the sampling data is shared by at least two of the data segments.

An emotion deciding unit configured to decide at least one of a user's representative emotion, a user's complex emotion, and a user's changed emotion based on the emotional segments.

The emotional segment creator is further configured to calculate a plurality of probability values of a plurality of candidate emotions for each of the respective data segments, and extract a candidate emotion having a greatest probability value from among the candidate emotions to decide the extracted candidate emotion as an emotional segment of a corresponding data segment, for each of the respective data segments.

An emotion deciding unit configured to decide at least one of a user's representative emotion, a user's complex emotion, and a user's changed emotion based on the emotional segment.

The emotion deciding unit further includes a representative emotion deciding unit configured to decide at least one of the emotional segments as the user's representative emotion based on a degree of reliability of each of the respective emotional segments.

The degree of reliability includes at least one of a standard deviation and an entropy value of the probability values for a respective one of the data segments.

The emotion deciding unit further includes a complex emotion deciding unit configured to decide at least two of the emotional segments as the user's complex emotion based on a degree of reliability of each of the respective emotional segments.

The degree of reliability of each emotional segment is defined based on at least one of a standard deviation and an entropy value of the probability values for a respective one of the data segments.

The emotion deciding unit further includes a changed emotion deciding unit configured to decide a time-ordered arrangement of the emotional segments as the changed emotion.

In another general aspect, there is provided an emotion recognition method including extracting sampling data from input data for emotion recognition. The emotion recognition method further includes segmenting the sampling data into a plurality of data segments. The emotion recognition method further includes creating a plurality of emotional segments that include a plurality of emotions corresponding to each of the respective data segments.

The emotion recognition method further includes deciding at least one of a user's representative emotion, a user's complex emotion, and a user's changed emotion based on the emotional segments.

The emotion recognition method further includes calculating a plurality of probability values of a plurality of candidate emotions for each of the respective data segments.

The emotion recognition method further includes calculating at least one of a plurality of standard deviations and a plurality of entropy values of the probability values for each of the respective data segments.

The emotion recognition method further includes extracting a greatest standard deviation from the standard deviations, and/or a greatest entropy value from among the entropy values. The emotion recognition method further includes deciding an emotional segment of a data segment corresponding to at least one of the greatest standard deviation and the greatest entropy value as a user's representative emotion.

The emotion recognition method further includes extracting a standard deviation greater than a predetermined threshold from among the standard deviations, and/or an entropy value greater than a predetermined threshold from among the entropy values. The emotion recognition method further includes deciding an emotional segment of a data segment corresponding to at least one of the extracted standard deviation and the extracted entropy value as a user's representative emotion.

In yet another general aspect, there is provided an apparatus including a data segment generator configured to generate data segments based on input data for emotion recognition. The apparatus further includes an emotional segment generator configured to generate emotional segments that include emotions corresponding to the respective data segments. The apparatus further includes an emotion recognition controller configured to recognize an emotion of a user based on the emotional segments.

The apparatus further includes a sampling data generator configured to generate sampling data based on the input data. The data segment generator is further configured to generate the data segments based on the sampling data.

The emotion segment generator is further configured to determine probability values of candidate emotions for each of the respective data segments. The emotion recognition controller is further configured to determine at least one of standard deviations and entropy values of the probability values for each of the respective data segments.

The emotion recognition controller is further configured to recognize at least two of the emotional segments as a user's complex emotion based on predetermined criteria associated with at least one of the probability values, the standard deviations, and the entropy values.

Other features and aspects will be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Figure 1:
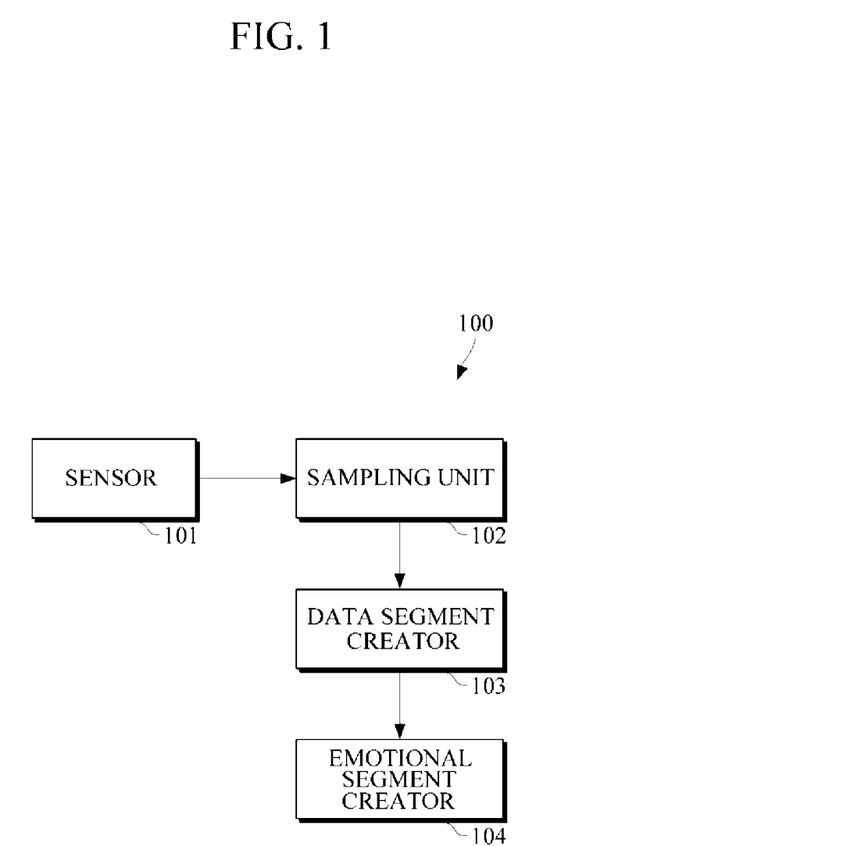
FIG. 1 is a diagram illustrating an example of an emotion recognition apparatus.

FIG. 1 is a diagram illustrating an example of an emotion recognition apparatus 100. The emotion recognition apparatus 100 may include a sensor 101, a sampling unit 102, a data segment creator 103, and an emotional segment creator 104.

The sensor 101 may measure and collect various kinds of input data to recognize a user's emotion. The input data may include various kinds of time-domain data related to the user. For example, the input data may include the user's facial image, the user's voice, text input by the user, the user's temperature, the user's location, a kind of an application being used by the user, etc. These input data are examples, and other input data may be used depending on the particular situation.

The sampling unit 102 may extract sampling data from the input data acquired by the sensor 101. For example, the sampling unit 102 may extract a portion of time-domain input data acquired by the sensor 101, using a predetermined size of a time-domain window. This process will be described in more detail with reference to FIG. 2 below.

Figure 2:
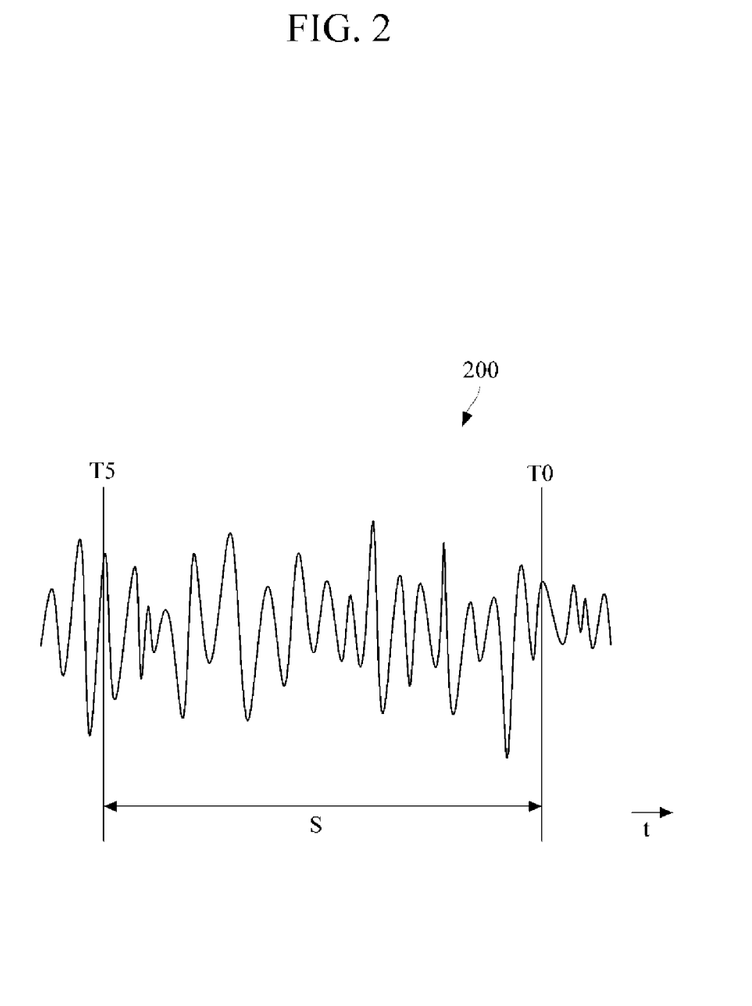
FIG. 2 is a waveform graph illustrating examples of input data and sampling data.

FIG. 2 is a waveform graph illustrating examples of input data 200 and sampling data S. The input data 200 acquired by the sensor 101 in FIG. 1 may be transferred to the sampling unit 102 in FIG. 1. For example, if the input data 200 is a voice signal, the X-axis may be a time (t), and the Y-axis may be a magnitude of the voice signal. The sampling unit 102 may extract the sampling data S in correspondence to a time period from a time point T0 to a time point T5, using a predetermined size of a time-domain window. The time period during which the sampling data S is extracted, a magnitude of the sampling data S, and the like, may vary depending on the purpose of an application.

Returning again to FIG. 1, the data segment creator 103 may segment the extracted sampling data S into a plurality of data segments. A data segment may be a portion or all of the sampling data S. For example, the data segment creator 103 may segment or reconfigure the sampling data S using a time-domain window having a size smaller than or equal to the sampling data S. In more detail, the data segment creator 103 may use a time-domain window to segment the sampling data S at regular intervals, or may use a plurality of time-domain windows having different sizes to segment the sampling data at different intervals. As another example, the data segment creator 103 may segment or reconfigure the sampling data S such that a portion of the sampling data S is shared by at least two data segments. These examples will be described in more detail with reference to FIGS. 3A, 3B, and 3C below.

Figure 3A:
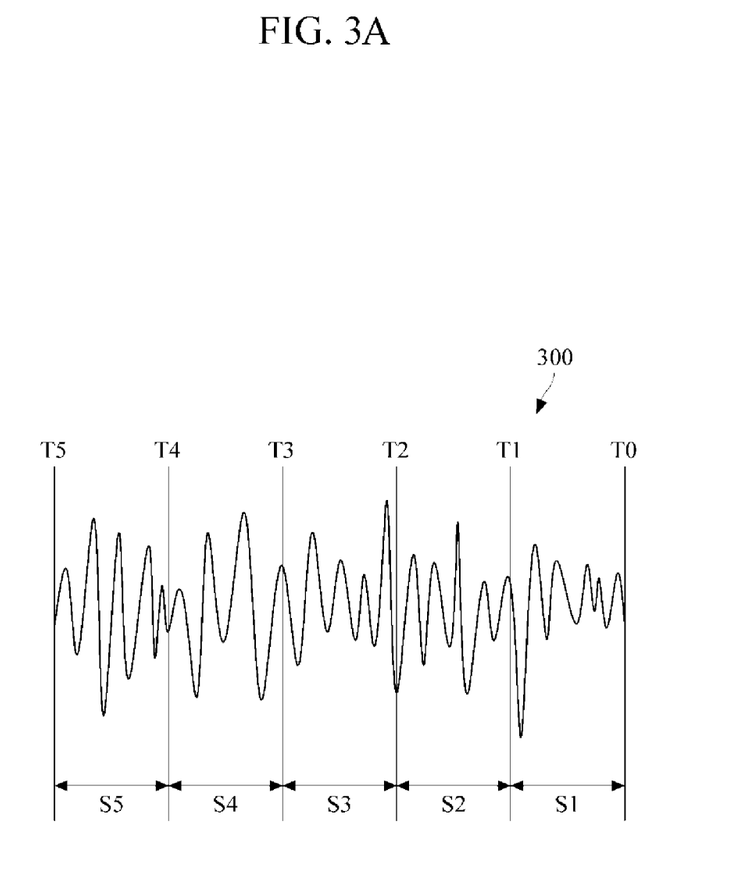
FIGS. 3A through 3C are waveform graphs illustrating examples of data segments.

FIGS. 3A through 3C are waveform graphs illustrating examples of data segments. Referring to FIGS. 1 and 3A, the data segment creator 103 may segment sampling data 300 at regular intervals to create a plurality of data segments S1 through S5 having the same size. For example, the data segment creator 103 may segment the sampling data 300 periodically during a time period from a time point T0 to a time point T5.

Figure 3B:
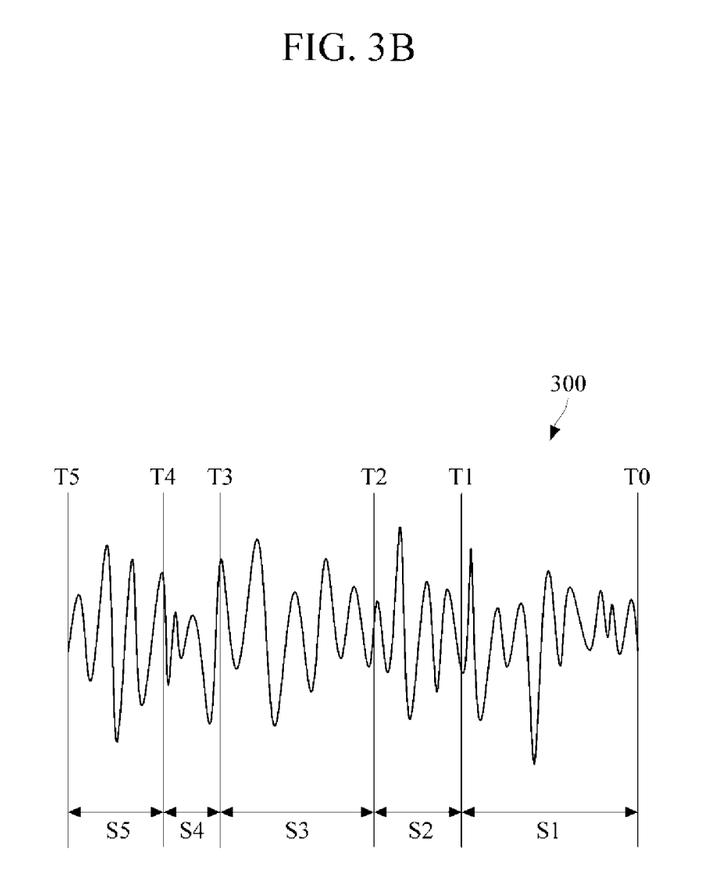

Referring to FIGS. 1 and 3B, the data segment creator 103 may segment the sampling data 300 at different intervals to create a plurality of data segments 51 through S5 having different sizes. For example, the data segment creator 103 may segment the sampling data 300 non-periodically during the time period from T0 to T5. FIG. 3B shows the case where the five data segments S1 through S5 all have different sizes, and is only an example. That is, in other examples, some of the data segments S1 through S5 may have the same size.

Figure 3C:
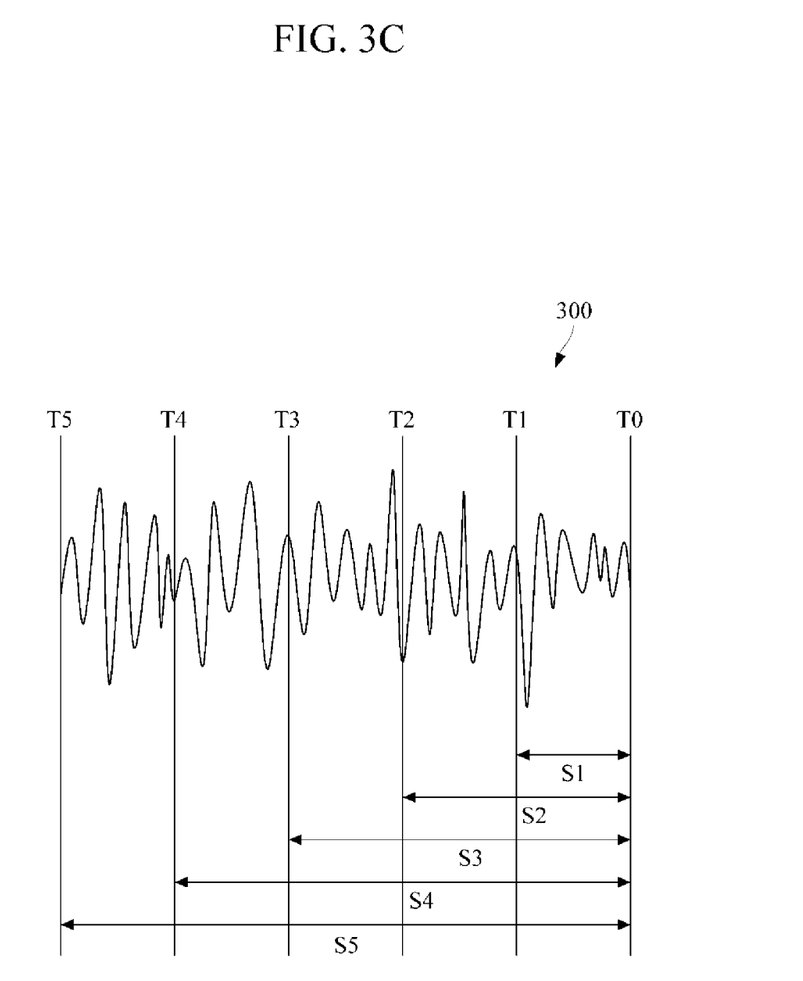

Referring to FIGS. 1 and 3C, the data segment creator 103 may create data segments S1 through S5 using an overlapping time-domain window such that a portion of sampling data 300 is shared by at least two data segments. For example, a time period corresponding to the data segment S1 may exist in the other data segments S2 through S5. In the current example, the overlapping time-domain window may represent two or more time-domain windows that share a specific time period. In other words, the data segment creator 103 may extract sampling data corresponding to a time period from T0 to T1 as a data segment S1, and again accumulatively extract sampling data corresponding to a time period from T0 to T2 as a data segment S2. FIG. 3C illustrates the case where the data segments S2 through S5 have sizes of integer multiples of the data segment S1. This is only an example, and it may be also possible to set more various sizes of time-domain windows. As such, the data segment creator 103 may segment the sampling data 300 using a non-overlapping time-domain window, or accumulatively segment the sampling data 300 using an overlapping time-domain window, to thereby represent or reconfigure the sampling data 300.

Returning again to FIG. 1, the emotional segment creator 104 may create an emotional segment for each data segment. The emotional segment may include an emotion (e.g., "Anger", "Happiness", etc.) corresponding to each data segment. The emotional segment creator 104 may recognize or detect emotional information corresponding to each data segment based on various methods. For example, the emotional segment creator 104 may stochastically decide emotional information (that is, an emotional segment) about each data segment based on degrees of similarity between each data segment and predetermined emotional models. This process will be described in more detail with reference to FIG. 4 below.

Figure 4:
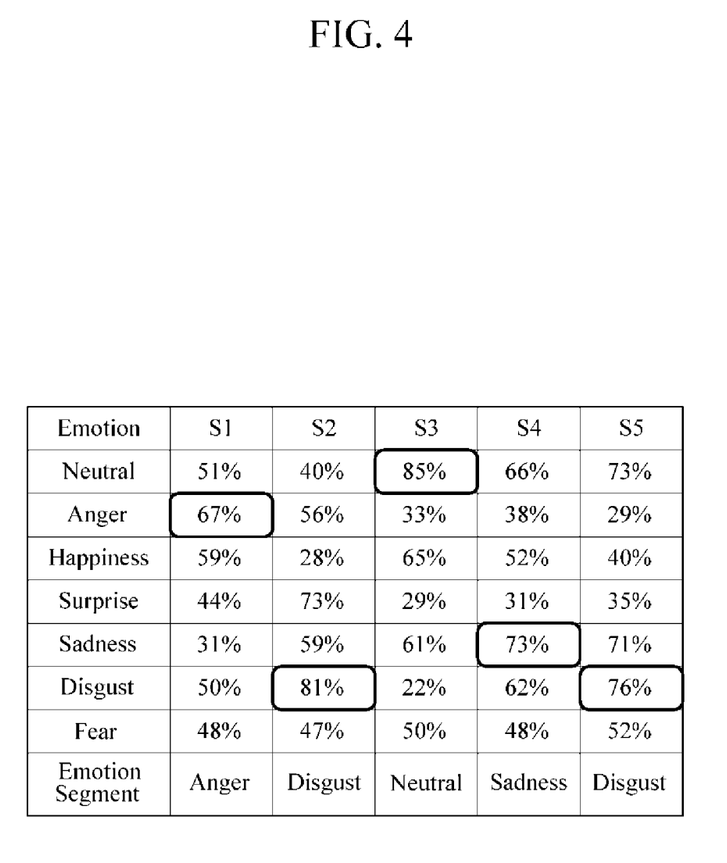
FIG. 4 is a table illustrating an example of an emotional segment creating method.

FIG. 4 is a table illustrating an example of an emotional segment creating method. The emotional segment creator 104 in FIG. 1 may stochastically decide an emotion corresponding to each data segment S1 through S5, e.g., in FIG. 3C. For example, the data segment S1 may be calculated to have probability values of 51%, 67%, 59%, 44%, 31%, 50%, and 48% in correspondence to candidate emotions of "Neutral", "Anger", "Happiness", "Surprise", "Sadness", "Disgust", and "Fear", respectively. Here, the probability value of each candidate emotion may be calculated based on a degree of similarity between the data segment S1 and predetermined model data about the candidate emotion, e.g., a "Happiness" facial image group including representative expressions that tend to appear when humans are in a happy emotional state. The specific percentages and emotions listed above are only examples, and other percentages and emotions may be used depending on the particular situation.

After the probability values for the individual kinds of emotions are all calculated, the emotional segment creator 104 may decide the emotion having the greatest probability value as an emotional segment of the corresponding data segment. For example, an emotional segment of the data segment Si may be decided as "Anger". This method of stochastically deciding the emotion is only an example, and emotional information of each data segment may be decided by a method of using a pattern or rule of input values, a method of using a neutral network, etc.

Returning again to FIG. 1, the emotional recognition apparatus 100 may be implemented as an electrical circuit and/or hardware that is installed in a specific terminal, and/or as a processor module or an application program that is included or installed in a specific terminal. The terminal may include, for example, a mobile terminal, such as a smart phone, or a fixed terminal, such as a personal computer. Also, the blocks illustrated in FIG. 1 may be functional blocks classified according to their logical functions. Accordingly, the functions of the emotion recognition apparatus 100 may be classified according to different criterion. Further, the functional blocks may be separately implemented, or two or more of the functional blocks may be integrated. Furthermore, a portion of functions of a functional block may be performed by one or more other functional blocks.

Figure 5:
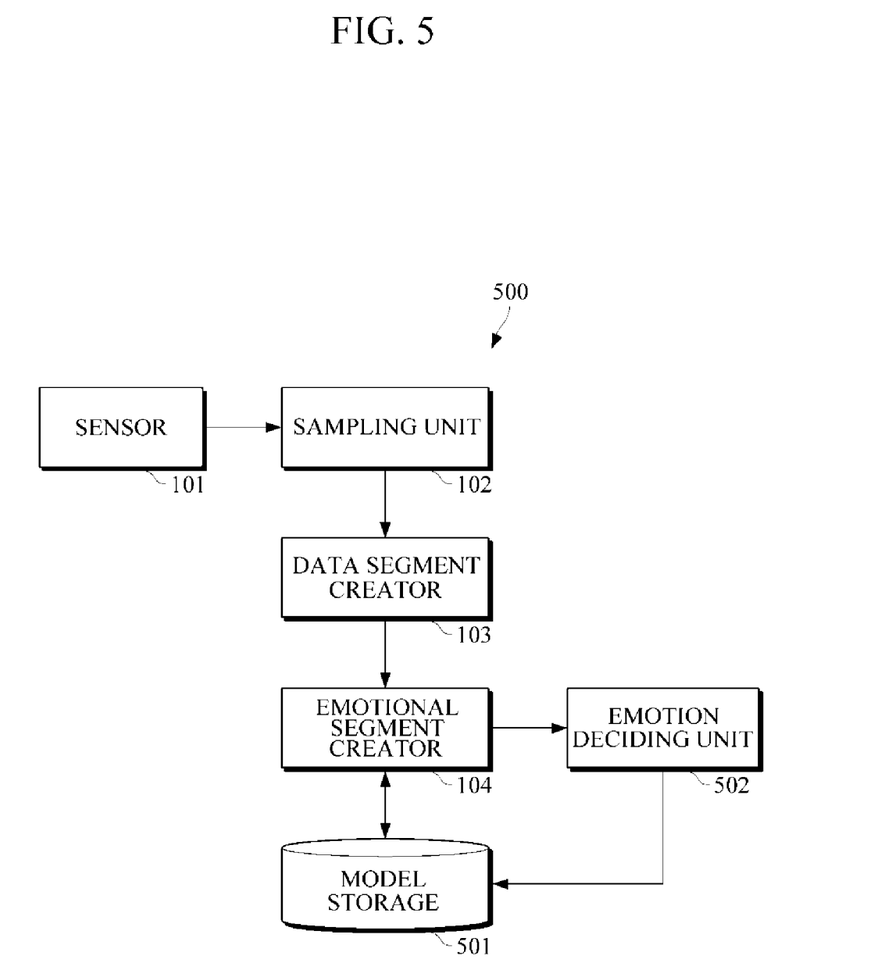
FIG. 5 is a diagram illustrating another example of an emotion recognition apparatus.

FIG. 5 is a diagram illustrating another example of an emotion recognition apparatus 500. The emotion recognition apparatus 500 may include the sensor 101, the sampling unit 102, the data segment creator 103, the emotional segment creator 104, a model storage 501, and an emotion deciding unit 502. Here, the sensor 101, the sampling unit 102, the data segment creator 103, and the emotional segment creator 104 may be the same as those described above in FIG. 1, and accordingly, detailed descriptions thereof will be omitted.

In FIG. 5, the model storage 501 may store predetermined data modeled according to a type of each emotion. For example, if the emotion recognition apparatus 500 uses a user's facial image, the model storage 501 may store a "sad" facial image group including representative expressions that tend to appear when humans are in a sad emotional state, a "happiness" facial image group including representative expressions that tend to appear when humans are in a happy emotional state, etc. Accordingly, the emotional segment creator 104 may compare each data segment to the modeled data to calculate a degree (e.g., a probability value) of similarity between the data segment and the modeled data. Also, after a user's emotion is decided by the emotion deciding unit 502, the model storage 501 may learn the decided emotion and update the modeled data.

The emotion deciding unit 502 may decide at least one of the user's representative emotion, the user's complex emotion, and the user's changed emotion based on a plurality of emotional segments obtained by the emotional segment creator 104. That is, since a human's emotions are complicated and change rapidly, the emotion deciding unit 502 may decide one of the emotional segments as the representative emotion, or two or more of the emotional segments as the complex emotion. Also, the emotion deciding unit 502 may arrange the emotional segments in an order of time (i.e., a series) to decide the changed emotion (that is, a change in emotion). The deciding of the representative emotion, the complex emotion, and the changed emotion will be described in more detail with reference to FIGS. 7A through 7C below.

Figure 6:
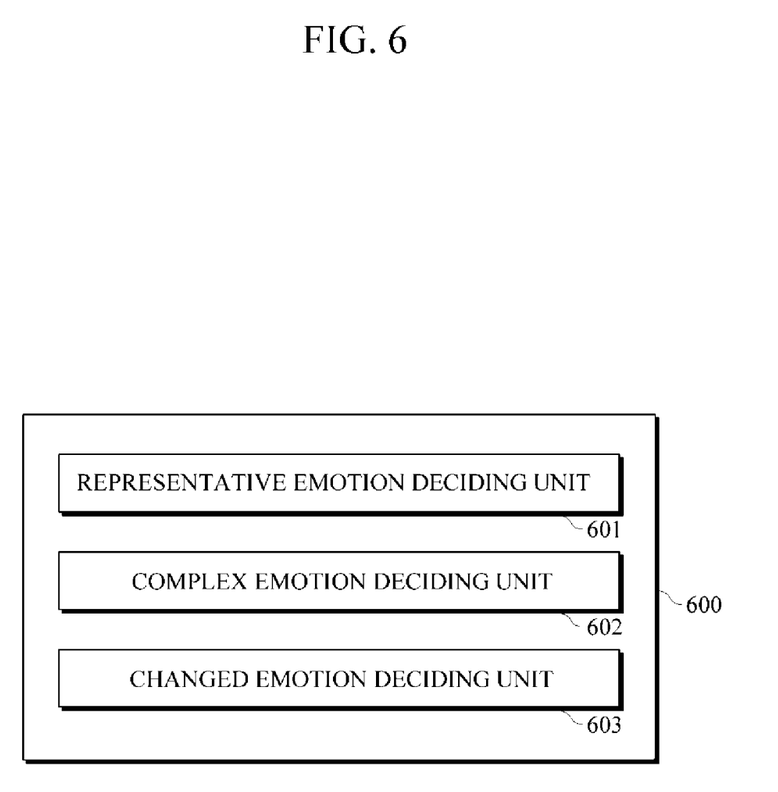
FIG. 6 is a diagram illustrating an example of an emotion deciding unit.

FIG. 6 is a diagram illustrating an example of an emotion deciding unit 600. The emotion deciding unit 600 may include a representative emotion deciding unit 601, a complex emotion deciding unit 602, and a changed emotion deciding unit 603. FIG. 6 shows, for convenience of description, an example where the emotion deciding unit 600 includes three functional blocks, and it may be also possible that only one or two of the functional blocks are selectively provided since the functional blocks operate independently from each other.

The representative emotion deciding unit 601 may decide at least one emotional segment as a representative emotion of sampling data according to a degree of reliability of each emotional segment. The complex emotion deciding unit 602 may decide at least two emotional segments as a complex emotion of the sampling data according to the degree of reliability of each emotional segment. The degree of reliability of each emotional segment may include a standard deviation or entropy of emotional probability values corresponding to each data segment. The changed emotion deciding unit 603 may decide a time-ordered series of emotional segments as a changed emotion. The deciding of the representative emotion, the complex emotion, and the changed emotion will be described in more detail with reference to FIGS. 7A through 7C below.

Figure 7A:
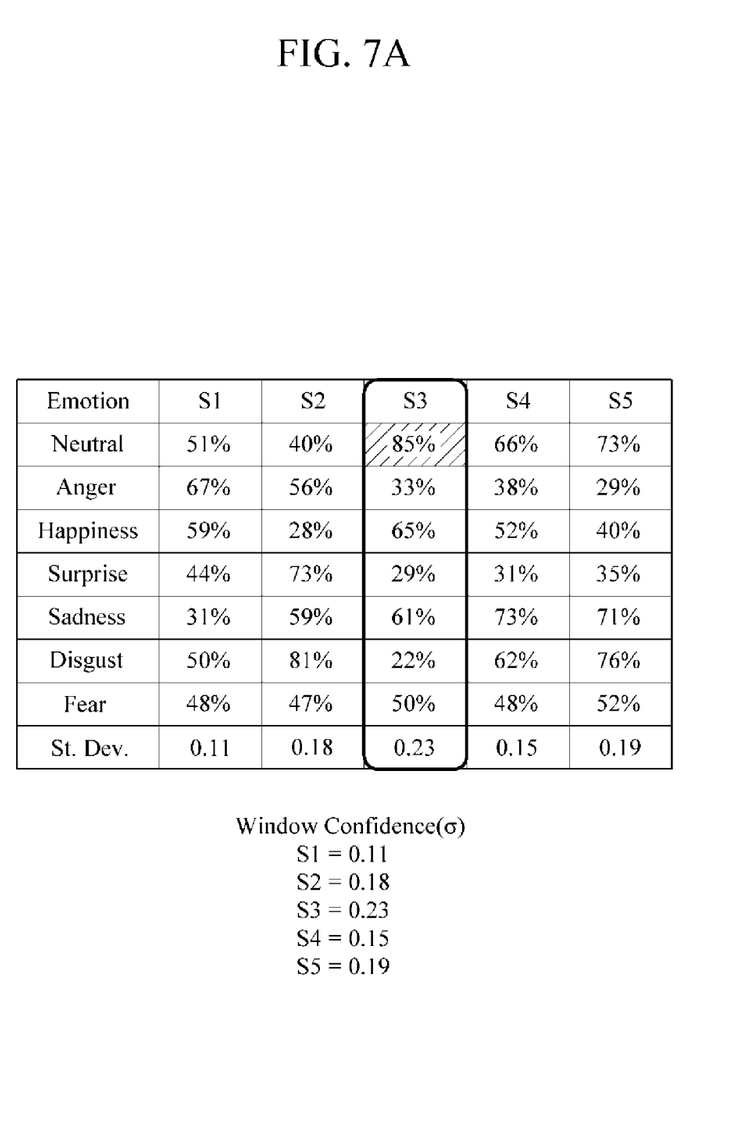
FIGS. 7A through 7C are tables illustrating an example of an emotion deciding method that is performed by the emotion deciding unit.
Figure 7B:
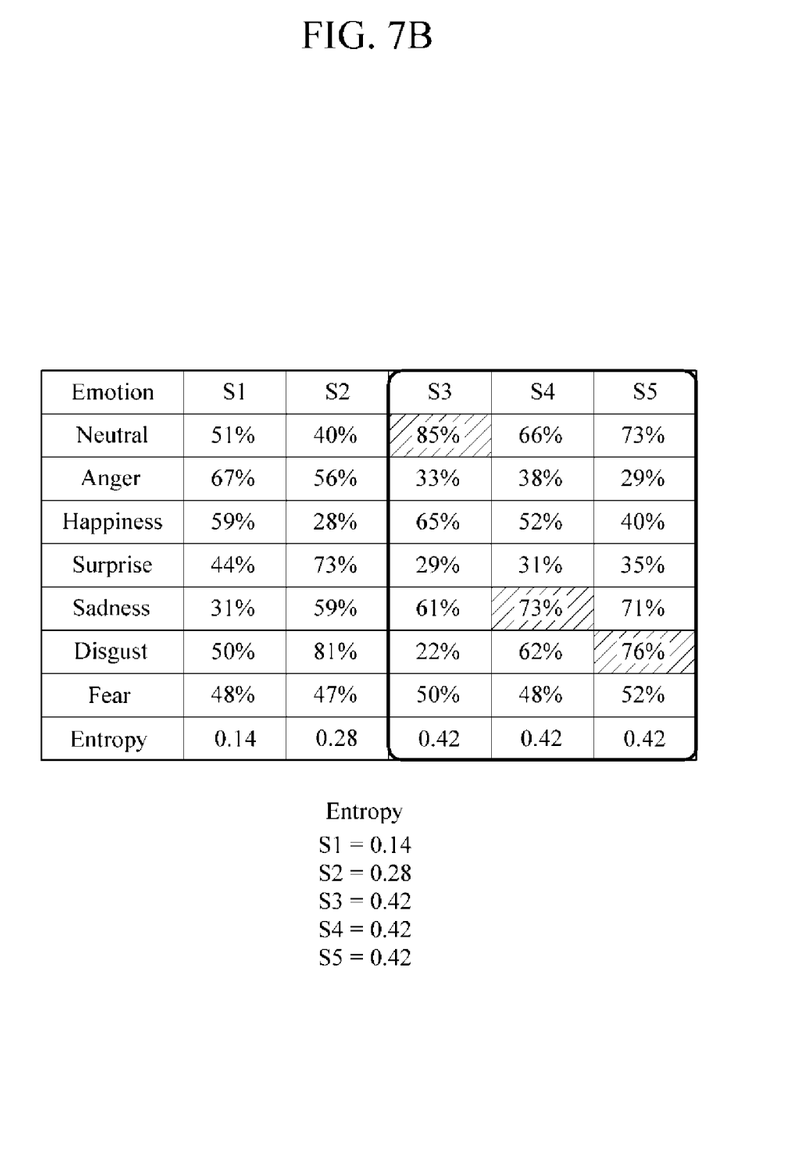
Figure 7C:
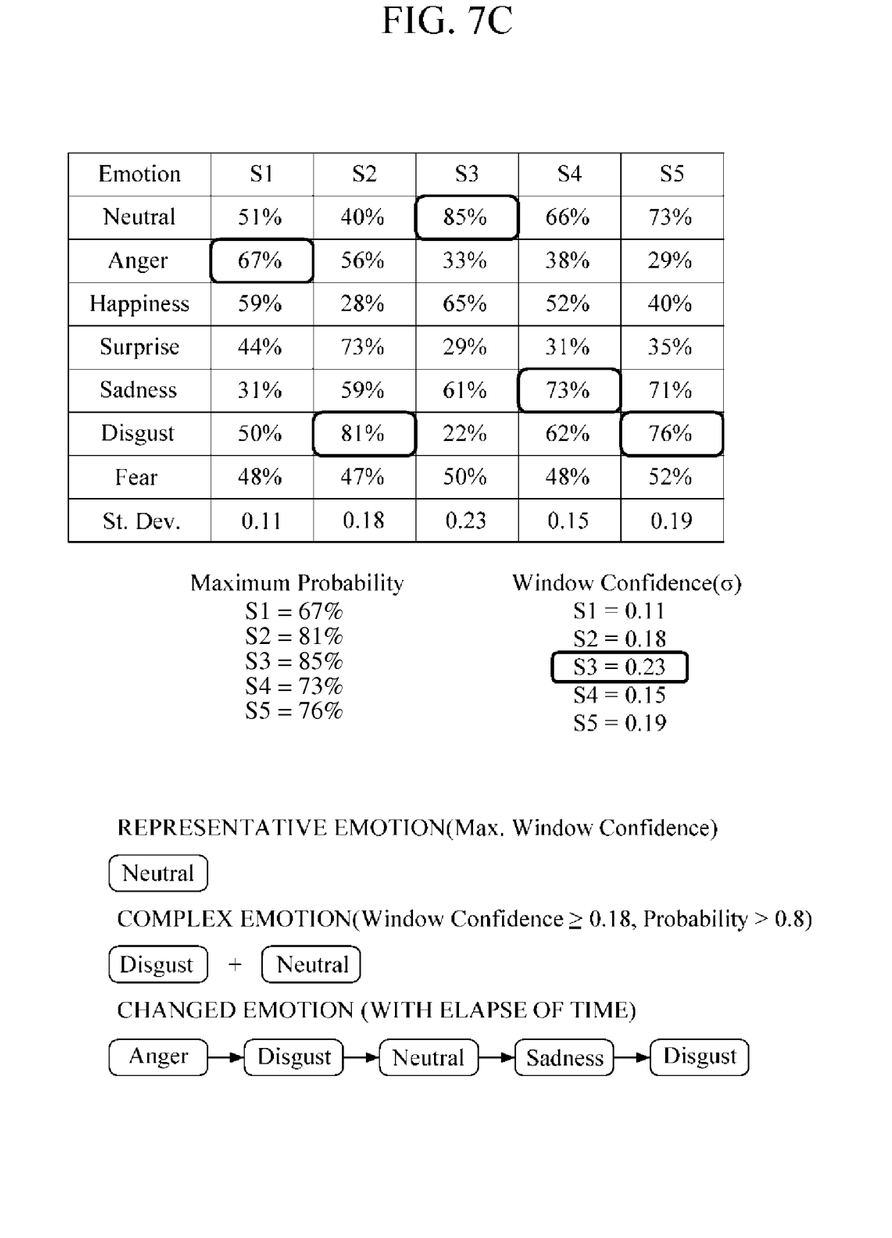

FIGS. 7A through 7C are tables illustrating an example of an emotion deciding method that is performed by the emotion deciding unit 600. Referring to FIGS. 6 and 7A, the representative emotion deciding unit 601 may calculate standard deviations (e.g., window confidences) of emotional probability values for each data segment 51 through S5. For example, the standard deviation of 0.23 may be calculated for the emotional probability values of the data segment S3. The specific standard deviations mentioned above and in FIG. 7A are only examples, and other standard deviations may be calculated depending on the particular situation.

The representative emotion deciding unit 601 may extract the greatest standard deviation, or the standard deviation greater than a predetermined threshold value, from among the calculated standard deviations. The representative emotion deciding unit 601 may decide an emotional segment of a data segment corresponding to the extracted standard deviation as a user's representative emotion. For example, if the data segment S3 has the greatest standard deviation (e.g., 0.23), the representative emotion deciding unit 601 may decide the emotional segment "Neutral" of the data segment S3 as the corresponding user's representative emotion. The decided representative emotion "Neutral" may be decided as the user's representative emotion during a time period from T0 to T5 in the example of, e.g., FIG. 2. In other words, the user may be considered to be in a "Neutral" emotional state during the time period from T0 to T5.

Referring to FIGS. 6 and 7B, the representative emotion deciding unit 601 may calculate entropy values of emotional probability values for each data segment 51 through S5. For example, the entropy values of 0.42 may be calculated for the emotional probability values of the data segments S3 through S5. The specific entropy values mentioned above and in FIG. 7B are only examples, and other entropy values may be calculated depending on the particular situation.

The representative emotion deciding unit 601 may extract the greatest entropy value, or the entropy value greater than a predetermined threshold value, from among the calculated entropy values. The representative emotion deciding unit 601 may decide an emotional segment of a data segment corresponding to the extracted entropy value as a user's representative emotion. For example, "Neutral is the representative emotional segment of the data segment S3 having the greatest entropy value (e.g., 0.42), and thus, may be decided as the user's representative emotion. The decided representative emotion may be decided as the user's representative emotion during the time period from T0 to T5 in the example of, e.g., FIG. 2. That is, the user may be considered to be in a "Neutral" emotional state during the time period from T0 to T5.

In another example, "Neutral", "Sadness", and "Disgust" are the emotional segments of the data segments S3, S4, and S5, respectively, whose entropy values (e.g., 0.42) are greater than a predetermined threshold value 0.3, and thus, any one of these emotional segments may be decided as the user's representative emotion. The decided representative emotion may be decided as the user's representative emotion during the time period from T0 to T5 in the example of, e.g., FIG. 2. For example, if "Disgust" is selected, the user may be considered to be in a "Disgust" emotional state during the time period from T0 to T5.

Referring to FIGS. 6 and 7C, the complex emotion deciding unit 602 may calculate standard deviations (e.g., window confidences) of emotional probability values for each data segment S1 through S5. For example, the standard deviation of 0.23 may be calculated for the emotional probability values of the data segment S3. The specific standard deviations mentioned above and in FIG. 7C are only examples, and other standard deviations may be calculated depending on the particular situation.

The complex emotion deciding unit 602 may decide at least two emotional segments of the respective data segments 51 through S5 as a user's complex emotion according to predetermined criteria. For example, if the predetermined criteria is a standard deviation greater than or equal to 0.18 and a probability value greater than 80%, the emotional segments "Disgust" and "Neutral", whose probability values are greater than 80%, of the respective data segments S2 and S3, may be decided as the user's complex emotion. The current example relates to the case where the complex emotion deciding unit 602 uses standard deviations to decide a complex emotion. It may be also possible that the complex emotion deciding unit 602 uses entropy values or various kinds of information relating to a degree of reliability of each emotional probability value to decide a complex emotion. The decided emotional segments may be decided as the user's complex emotion during the time period from T0 to T5 in the example of, e.g., FIG. 2. In other words, the user may be considered to be in a complex emotional state where "Disgust" and "Neutral" are mixed during the time period from T0 to T5.

In another example, the changed emotion deciding unit 603 may arrange a plurality of emotional segments in an order of time (i.e., a series) to thereby decide a changed emotion that represents changes in a user's emotion. For example, if the data segment creator 103 of FIG. 1 creates a plurality of data segments S1 through S5 as shown in, e.g., FIG. 3C, changes in the user's emotion may be represented as "Anger", "Disgust", "Neutral", "Sadness", "Disgust", etc., during a time period from T0 to T5. That is, the user's emotion may be considered to change in an order of "Anger", "Disgust", Neutral", "Sadness", and "Disgust" during the time period from T0 to T5 in the example of, e.g., FIG. 2.

Figure 8:
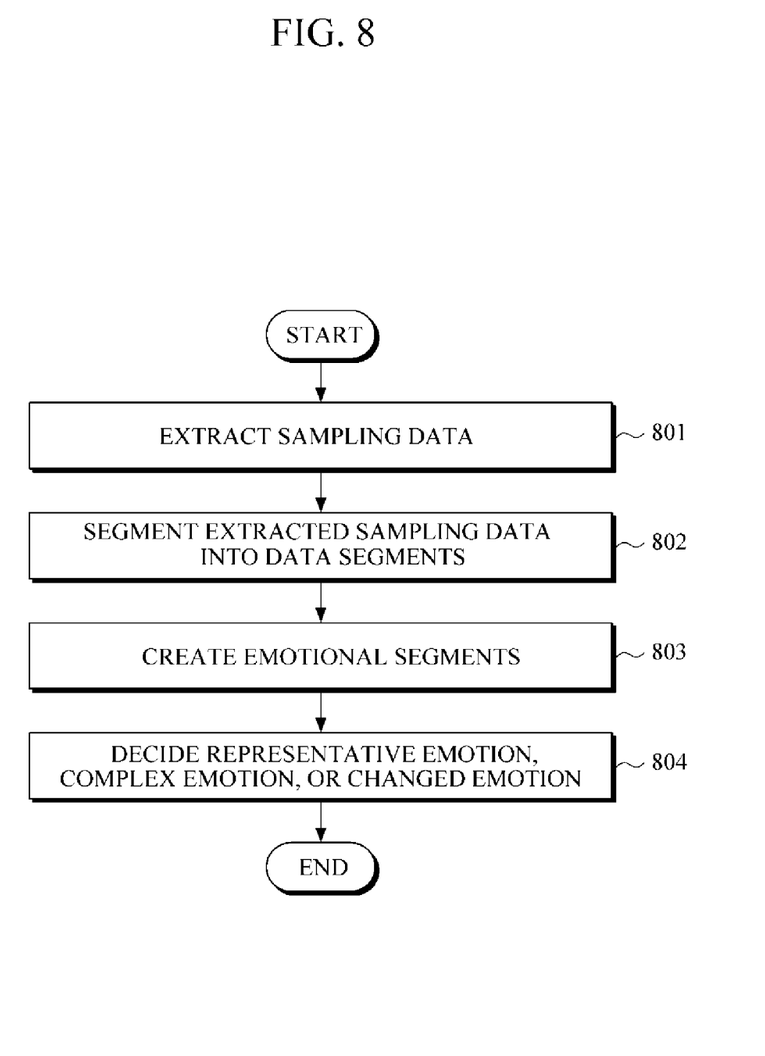
FIG. 8 is a flowchart illustrating an example of an emotion recognition method based on emotional segments.

FIG. 8 is a flowchart illustrating an example of an emotion recognition method based on emotional segments. At step 801, the emotional recognition apparatus 500 in FIG. 5 may extract sampling data from input data. For example, the sampling unit 102 in FIG. 5 may is extract the sampling data as shown in FIG. 2.

At step 802, the emotion recognition apparatus 500 may segment the extracted sampling data into a plurality of data segments. For example, the data segment creator 103 in FIG. 5 may segment and reconfigure the sampling data into the plurality of data segments as illustrated in FIGS. 3A through 3C.

At step 803, the emotion recognition apparatus 500 may create emotional segments in correspondence to each data segment. For example, the emotional segment creator 104 in FIG. 5 may stochastically decide the emotions for each data segment, as shown in FIG. 4.

At step 804, the emotion recognition apparatus 500 may decide a representative emotion, a complex emotion, or a changed emotion. For example, the emotion deciding unit 502 in FIG. 5 may decide the representative emotion, the complex emotion, the changed emotion, etc., using the emotional segments as shown in FIGS. 7A through 7C.

Therefore, according to the examples as described above, there is provided an apparatus and method to recognize a user's emotion based on emotional segments, which may more efficiently and correctly interpret a human's complex emotion. Accordingly, an appropriate service may be provided according to the user's emotional state.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of non-transitory computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

As a non-exhaustive illustration only, a terminal described herein may refer to mobile devices such as a cellular phone, a personal digital assistant (PDA), a digital camera, a portable game console, and an MP3 player, a portable/personal multimedia player (PMP), a handheld e-book, a portable laptop PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An emotion recognition apparatus comprising:
at least one processor;
a sampling unit of the at least one processor configured to extract, from input data for emotion recognition, sampling data corresponding to a time period, wherein the input data comprises a facial image of a user, a voice of the user, text input by the user, a temperature of the user, a location of the user, or a kind of an application being used by the user;
a data segment creator of the at least one processor configured to accumulatively segment the sampling data, based on one or more predetermined time-domain windows, to form a plurality of data segments, wherein each of the data segments subsequent to a first data segment, among the plurality of data segments, includes portions of the sampling data from a current sampling time period and all previous sampling time periods;
an emotional segment creator of the at least one processor configured to create a plurality of emotional segments that comprise a plurality of emotions corresponding to each of the respective data segments; and
an emotion deciding unit of the at least one processor comprising a complex emotion deciding unit configured to decide at least two of the emotional segments as the user's complex emotion.

2. The emotion recognition apparatus of claim 1, wherein the data segment creator is further configured to segment the sampling data at regular intervals based on a predetermined time-domain window.

3. The emotion recognition apparatus of claim 1, wherein the data segment creator is further configured to segment the sampling data at different intervals based on two or more predetermined time-domain windows.

4. The emotion recognition apparatus of claim 1, wherein the data segment creator is further configured to reconfigure the sampling data based on a predetermined time-domain window such that the portion of the sampling data is shared by the at least two of the data segments.

5. The emotion recognition apparatus of claim 1, wherein the emotion deciding unit is further configured to decide at least one of a user's representative emotion and a user's changed emotion based on the emotional segments.

6. The emotion recognition apparatus of claim 1, wherein the emotional segment creator is further configured to:
calculate a plurality of probability values of a plurality of candidate emotions for each of the respective data segments, and
extract a candidate emotion having a greatest probability value from among the candidate emotions to decide the extracted candidate emotion as an emotional segment of a corresponding data segment, for each of the respective data segments.

7. The emotion recognition apparatus of claim 1, wherein the emotion deciding unit further comprises a representative emotion deciding unit configured to decide at least one of the emotional segments as the user's representative emotion based on a degree of reliability of each of the respective emotional segments.

8. The emotion recognition apparatus of claim 7, wherein the degree of reliability comprises at least one of a standard deviation and an entropy value of the probability values for a respective one of the data segments.

9. The emotion recognition apparatus of claim 1, wherein the complex emotion deciding unit is configured to decide at least two of the emotional segments as the user's complex emotion based on a degree of reliability of each of the respective emotional segments.

10. The emotion recognition apparatus of claim 9, wherein the degree of reliability of each emotional segment is defined based on at least one of a standard deviation and an entropy value of the probability values for a respective one of the data segments.

11. The emotion recognition apparatus of claim 1, wherein the emotion deciding unit further comprises a changed emotion deciding unit configured to decide a time-ordered arrangement of the emotional segments as the changed emotion.

12. An emotion recognition method comprising:
using a processor, extracting, from input data for emotion recognition, sampling data corresponding to a time period, wherein the input data comprises a facial image of a user, a voice of the user, text input by the user, a temperature of the user, a location of the user, or a kind of an application being used by the user;
using the processor, accumulatively segmenting the sampling data based on one or more predetermined time-domain windows to form a plurality of data segments, wherein each of the data segments subsequent to a first data segment, among the plurality of data segments, includes portions of the sampling data from a current sampling time period and all previous sampling time periods;

creating, using the processor, a plurality of emotional segments that comprise a plurality of emotions corresponding to each of the respective data segments; and deciding, using the processor, at least two emotional segments of the respective data segments as the user's complex emotion.

13. The emotion recognition method of claim 12, further comprising deciding at least one of a user's representative emotion and a user's changed emotion based on the emotional segments.

14. The emotion recognition method of claim 12, further comprising calculating a plurality of probability values of a plurality of candidate emotions for each of the respective data segments.

15. The emotion recognition method of claim 14, further comprising calculating at least one of a plurality of standard deviations and a plurality of entropy values of the probability values for each of the respective data segments.

16. The emotion recognition method of claim 15, further comprising:

extracting a greatest standard deviation from the standard deviations, and/or a greatest entropy value from among the entropy values; and deciding an emotional segment of a data segment corresponding to at least one of the greatest standard deviation and the greatest entropy value as a user's representative emotion.

17. The emotion recognition method of claim 15, further comprising:

extracting a standard deviation greater than a predetermined threshold from among the standard deviations, and/or an entropy value greater than a predetermined threshold from among the entropy values; and deciding an emotional segment of a data segment corresponding to at least one of the extracted standard deviation and the extracted entropy value as a user's representative emotion.

18. An apparatus comprising:

at least one processor;

a data segment generator of the at least one processor configured to extract sampling data corresponding to a time period and to accumulatively generate data segments, at one or more predetermined time-domain windows, based on input data for emotion recognition, wherein the input data comprises a facial image of a user, a voice of the user, text input by the user, a temperature of the user, a location of the user, or a kind of an application being used by the user, and each of the data segments subsequent to a first data segment of the data segments includes portions of the sampling data from a current sampling time period and all previous sampling time periods;

an emotional segment generator of the at least one processor configured to generate emotional segments that comprise emotions corresponding to the respective data segments; and an emotion recognition controller configured to recognize an emotion of a user based on the emotional segments and to recognize at least two of the emotional segments as the user's complex emotion.

19. The apparatus of claim 18, further comprising:

a sampling data generator configured to generate the sampling data based on the input data, wherein the data segment generator is further configured to generate the data segments based on the sampling data.

20. The apparatus of claim 18, wherein:

the emotion segment generator is further configured to determine probability values of candidate emotions for each of the respective data segments; and the emotion recognition controller is further configured to determine at least one of standard deviations and entropy values of the probability values for each of the respective data segments.

21. The apparatus of claim 20, wherein the emotion recognition controller is configured to recognize at least two of the emotional segments as a user's complex emotion based on predetermined criteria associated with at least one of the probability values, the standard deviations, and the entropy values.

* * * * *